US008621346B2

(12) United States Patent
Ikeda et al.

(10) Patent No.: US 8,621,346 B2
(45) Date of Patent: Dec. 31, 2013

(54) MEDICAL IMAGE DIAGNOSIS APPARATUS, SECURITY MANAGING SYSTEM, AND SECURITY MANAGING METHOD

(75) Inventors: Satoshi Ikeda, Yaita (JP); Fumiaki Teshima, Nasushiobara (JP)

(73) Assignees: Kabushiki Kaisha Toshiba, Tokyo (JP); Toshiba Medical Systems Corporation, Otawara-Shi (JP)

( * ) Notice: Subject to any disclaimer, the term of this patent is extended or adjusted under 35 U.S.C. 154(b) by 1657 days.

(21) Appl. No.: 11/575,541

(22) PCT Filed: Nov. 18, 2005

(86) PCT No.: PCT/JP2005/021248
§ 371 (c)(1),
(2), (4) Date: Mar. 19, 2007

(87) PCT Pub. No.: WO2006/054699
PCT Pub. Date: May 26, 2006

(65) Prior Publication Data
US 2008/0004506 A1 Jan. 3, 2008

(30) Foreign Application Priority Data
Nov. 19, 2004 (JP) .................................. 2004-336349

(51) Int. Cl.
*G06F 17/00* (2006.01)

(52) U.S. Cl.
USPC ........................................................ 715/272

(58) Field of Classification Search
USPC ................................................. 715/867, 272
See application file for complete search history.

(56) References Cited

U.S. PATENT DOCUMENTS

| 5,107,443 | A | * | 4/1992 | Smith et al. | 715/751 |
|---|---|---|---|---|---|
| 5,801,697 | A | * | 9/1998 | Parikh et al. | 715/790 |
| 6,424,332 | B1 | | 7/2002 | Powell | |
| 6,590,597 | B1 | | 7/2003 | Kim | |
| 6,738,081 | B2 | * | 5/2004 | Gupta et al. | 715/767 |
| 7,428,701 | B1 | * | 9/2008 | Gavin et al. | 715/243 |
| 7,634,455 | B1 | * | 12/2009 | Keene et al. | 1/1 |
| 2003/0107584 | A1 | * | 6/2003 | Clapper | 345/619 |
| 2003/0142133 | A1 | * | 7/2003 | Brown et al. | 345/768 |
| 2004/0153675 | A1 | * | 8/2004 | Dorn et al. | 713/202 |

(Continued)

FOREIGN PATENT DOCUMENTS

| EP | 1 191 342 A2 | 3/2002 |
|---|---|---|
| EP | 1 191 342 A3 | 3/2002 |

(Continued)

*Primary Examiner* — Frank D Mills
(74) *Attorney, Agent, or Firm* — Oblon, Spivak, McClelland, Maier & Neustadt, L.L.P.

(57) ABSTRACT

A medical image diagnostic apparatus includes: a screen saver shape storing unit that stores shapes of a screen saver for respective execution states of an application; a screen saver activation event detecting unit that detects an event serving as an activation condition for the screen saver; an application execution state detecting unit that detects an execution state of the application; a screen saver screen creating unit that reads a shape of the screen saver corresponding to the execution state of the application from the screen saver shape storing unit and creates screen saver image information; and a screen saver managing unit that receives notification indicating that the event serving as the activation condition for the screen saver is detected and requests detection of the execution state of the application and, on the other hand, give the application execution state information to the screen saver screen creating unit to request creation of the screen saver image information.

14 Claims, 14 Drawing Sheets

(56) References Cited

U.S. PATENT DOCUMENTS

| | | |
|---|---|---|
| 2005/0052446 A1* | 3/2005 | Plut .............................. 345/211 |
| 2005/0060670 A1* | 3/2005 | Inui et al. ..................... 715/867 |
| 2005/0086515 A1* | 4/2005 | Paris ............................. 713/200 |
| 2005/0222876 A1* | 10/2005 | Iwayama et al. ................ 705/3 |

FOREIGN PATENT DOCUMENTS

| | | |
|---|---|---|
| EP | 1 191 342 A8 | 3/2002 |
| EP | 1 410 761 A1 | 4/2004 |
| EP | 1 420 354 A2 | 5/2004 |
| EP | 1 420 354 A3 | 5/2004 |
| JP | 7-121336 | 5/1995 |
| JP | 2002-229538 | 8/2002 |
| JP | 2003-211799 | 7/2003 |
| JP | 2003-290196 | 10/2003 |
| JP | 2003290196 A * | 10/2003 |
| JP | 2004-89312 | 3/2004 |
| WO | WO 93/01574 | 1/1993 |
| WO | WO 03/030069 A1 | 4/2003 |

* cited by examiner

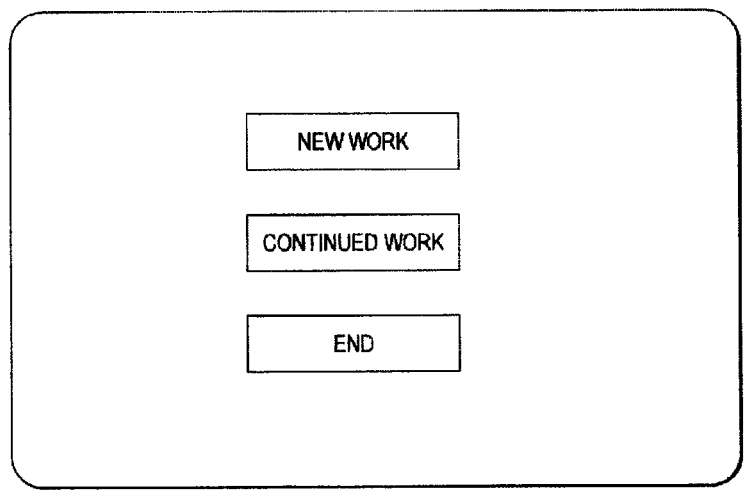

FIG. 5

| RECONFIGURATION: 0 | NAME: |
| IMAGE TRANSFER: 0 | AGE: |
| | SEX: |
| | RESERVATION DATE AND TIME: |
| | TEST PURPOSE: |

BED

☑ ADULT    PHOTOGRAPHING PLAN    [START] [ABORT]
☑ CHEST

FIG. 6

RECONFIGURATION: 0
HD CAPACITY: 60%

IMAGE

WL
WW

STUDY

| ID | TEST DATE | NAME | SEX |
|----|-----------|------|-----|
|    |           |      |     |
|    |           |      |     |

STUDY

| ID | IMG | POSTURE | DIRECTION |
|----|-----|---------|-----------|
|    |     |         |           |
|    |     |         |           |

STUDY

| ID | SCAN TIME | SLICE WIDTH |
|----|-----------|-------------|
|    |           |             |
|    |           |             |

[COPY]  [DELETE]  [PROTECT]

| APPLICATION EXECUTION STATE | SCREEN DATA |
|---|---|
| PATIENT REGISTRATION | AAA. BMP |
| IMAGE PHOTOGRAPHING | BBB. JPG |

| APPLICATION EXECUTION STATE | | SCREEN DATA |
|---|---|---|
| PATIENT REGISTRATION | DOCTOR | AAA. BMP |
| PATIENT REGISTRATION | ENGINEER | AA2. BMP |
| IMAGE PHOTOGRAPHING | DOCTOR | BBBB.JPG |

FIG. 12

| APPLICATION EXECUTION STATE | | SCREEN VERTEX DATA |
|---|---|---|
| PATIENT REGISTRATION | DOCTOR | (100, 900) (100, 0) (0, 400) (400, 500) (700, 500) (700, 900) |
| PATIENT REGISTRATION | ENGINEER | (100, 900) • • • • • |
| IMAGE PHOTOGRAPHING | DOCTOR | (100, 900) • • • • • |

FIG. 13

| APPLICATION EXECUTION STATE | | AREA NAME | DISPLAY/ NON-DISPLAY |
|---|---|---|---|
| PATIENT REGISTRATION | DOCTOR | PATIENT REGISTRATION | NON-DISPLAY |
| | | APPLICATION OPERATION AREA | NON-DISPLAY |
| | | APPARATUS STATUS AREA | DISPLAY |

MEDICAL IMAGE DIAGNOSIS APPARATUS, SECURITY MANAGING SYSTEM, AND SECURITY MANAGING METHOD

TECHNICAL FIELD

The present invention relates to a technique for securing security of information by causing an operation terminal to display a display shielding screen to conceal information that is unsuitable for people other than a specific user to inspect and, in particular, to a medical image diagnostic apparatus, a security managing system, and a security managing method that are capable of causing an operation terminal to display desired information, which plural users desire to inspect, in a desired display method according to conditions such as a status of the apparatus and authorities of the respective users even while display shielding is active.

BACKGROUND ART

Conventionally, in an operation terminal of a computer, when no operation is performed for a fixed time, a screen saver is activated to prevent the third party from easily inspecting information displayed on a monitor. Security management for information is performed by such a screen saver function.

The screen saver function is provided not only in a general-purpose computer but also in operation terminals included in various kinds of medical image diagnostic apparatuses and various apparatuses such as an analytical instrument. For example, a technique for providing a screen saver control function in an analytical instrument including a function of creating and rendering a graph from measurement data and, when, for example, no operation is performed for a certain fixed time during measurement, activating a screen saver according to the screen saver control function is devised (see, for example, Patent Document 1).

Moreover, a technique for providing, in this analytical instrument, a data processing device for analytical instruments that displays a latest graph result calculated by a chromatogram processing unit on a screen saver screen displayed on a monitor is devised. In this technique, a method of creating a screen saver screen using a graph and a method of pasting the graph on the screen saver screen are devised.

In a screen saver control technique in the conventional analytical instruments, only display of specific information such as a graph result is examined. In an apparatus that displays only a single image corresponding to a purpose such as the analytical instrument, it is possible to improve convenience of the apparatus by displaying specific information decided in advance on the screen saver.

However, when the screen saver function is provided in the operation terminal of the medical image diagnostic apparatus, things are different. The medical image diagnostic apparatus includes plural functions such as a registration function for photographed patient information, a medical image photographing function, a medical image observation function, and a filing function. Various images corresponding to the respective functions are displayed on the operation terminal of the medical image diagnostic apparatus. In general, usable functions vary depending on an attribute of a user of the medical image diagnostic apparatus, for example, whether the user is a doctor or a radio engineer.

Therefore, when the screen saver function is provided in the operation terminal of the medical image diagnostic apparatus, it is inappropriate to dynamically create a screen save screen using specific information decided in advance as in the technique used for the conventional analytical instrument. It is necessary to cause the operation terminal to arbitrarily define image information to be displayed while the screen saver is active according to a status of the medical image diagnostic apparatus and authorities of users. In this regard, such necessity is not taken into account at all in the screen saver control technique used in the conventional analytical instrument.

Incidentally, in a GUI (Graphical user interface) forming a basis of the screen saver control technique, in general, arrangement of display items of the GUI is determined on the basis of fixed rules. For example, a patient name is arranged on the upper left of a screen and an application execution button is arranged in a lower part of the screen. In this way, the display items such as execution buttons are arranged according to a fixed rule for each application type. This takes into account a characteristic that a color, a shape, and an arrangement position of an object affect object cognition of the human.

When such characteristic of a cognition ability of the human is considered, it is inappropriate as a control technique for a screen saver, which should be displayed on a screen of the operation terminal in the medical image diagnostic apparatus, to create a screen saver image simply using calculation in progress of a chromatograph as in the screen saver control technique used in the conventional analytical instrument. This is because, when the screen saver is used in the medical image diagnostic apparatus, it is necessary to display information, which has plural different meanings such as a processing progress state of an application and an examination request state, on the operation terminal while concealing privacy information of a patient such as a patient name from which the patient can be identified. Thus, depending on display positions of the respective kinds of information, it is likely that misunderstanding of a user is induced.

Therefore, when information is presented on the screen saver screen of the operation terminal in the medical image diagnostic apparatus, it is desirable that information is displayed on the screen saver screen in the same color and the same arrangement as a screen used by a user in his/her daily work. However, in the screen saver control technique used in the conventional analytical instrument, such display of information is not taken into account at all.

Patent Document 1: JP-A-2002-229538

DISCLOSURE OF THE INVENTION

The invention has been devised in order to cope with such conventional circumstances and it is an object of the invention to provide a medical image diagnostic apparatus, a security managing system, and a security managing method that are capable of securing security of information by causing an operation terminal to display a display shielding screen to conceal information that is unsuitable for people other than a specific user to inspect and, on the other hand, causing an operation terminal to display desired information, which plural users desire to inspect, in a desired display method according to conditions such as a status of the apparatus and authorities of the respective users even while display shielding is active.

In order to attain the object described above, the invention provides a medical image diagnostic apparatus that includes an operation terminal having an input device and a display device. The medical image diagnostic apparatus includes: a display shielding area information storing unit that stores information on an area in which display shielding is activated; a display shielding activation event detecting unit that detects an event serving as a condition for activating the display shielding; and a display shielding screen creating unit that reads, when the event is detected by the display shielding activation event detecting unit, the area information from the display shielding area information storing unit and creates display shielding screen information for causing the display device to display the display shielding on the basis of the area information read.

In order to attain the object, the invention provides a medical image diagnostic apparatus that includes an operation terminal having an input device and a display device. The medical image diagnostic apparatus includes: a screen saver shape storing unit that stores shapes of a screen saver for respective execution states of an application; a screen saver activation event detecting unit that detects an event serving as an activation condition for the screen saver; an application execution state detecting unit that detects an execution state of the application as application execution state information; a screen saver screen creating unit that reads a shape of the screen saver corresponding to the execution state of the application form the screen saver shape storing unit and creates screen saver image information for causing the display device to display the screen saver on the basis of the shape of the screen saver read; and a screen saver managing unit that receives notification indicating that the event serving as the activation condition for the screen saver is detected from the screen saver activation event detecting unit and request the application execution state detecting unit to detect the execution state of the application and, on the other hand, receives the application execution state information detected in the application execution state detecting unit and gives the application execution state information received to the screen saver screen creating unit to request the screen saver screen creating unit to create the screen saver image information.

In order to attain the object, the invention provides a security managing system that includes an operation terminal having an input device and a display device. The security managing system includes: a display shielding area information storing unit that stores information on an area in which display shielding is activated; a display shielding activation event detecting unit that detects an event serving as a condition for activating the display shielding; and a display shielding screen creating unit that reads, when the event is detected by the display shielding activation event detecting unit, the area information from the display shielding area information storing unit and created display shielding screen information for causing the display device to display the display shielding on the basis of the area information read.

In order to attain the object, the invention provides a security managing system that includes an operation terminal having an input device and a display device. The security managing system includes: a screen saver shape storing unit that stores shapes of a screen saver for respective execution states of an application; a screen saver activation event detecting unit that detects an event serving as an activation condition for the screen saver; an application execution state detecting unit that detects an execution state of the application as application execution state information; a screen saver screen creating unit that reads a shape of the screen saver corresponding to the execution state of the application from the screen saver shape storing unit and creates screen saver image information for causing the display device to display the screen saver on the basis of the shape of the screen saver read; and a screen saver managing unit that receives notification indicating that the event serving as the activation condition for the screen saver is detected from the screen saver activation event detecting unit and requests the application execution state detecting unit to detect the execution state of the application and, on the other hand, receives the application execution state information detected in the application execution state detecting unit and gives the application execution state information received to the screen saver screen creating unit to request the screen saver screen creating unit to create the screen saver image information.

In order to attain the object, the invention provides a security managing method that includes an operation terminal having an input device and a display device. The security managing method includes: a step of storing information on an area in which display shielding is activated; a step of detecting an event serving as a condition for activating the display shielding; and a step of reading, when the event is detected, the area information and creating display shielding screen information for causing the display device to display the display shielding on the basis of the area information read.

In order to attain the object, the invention provides a security managing method that includes an operation terminal having an input device and the display device. The security managing method includes: a step of storing shapes of a screen saver for respective execution states of an application; a step of detecting an event serving as an activation condition for the screen saver; a step of detecting an execution state of the application when the event serving as an activation condition for the screen saver is detected; and a step of creating screen saver image information for causing the display device to display the screen saver using a shape of the screen saver corresponding to the execution state of the application detected among the shapes of the screen saver stored.

In order to attain the object, the invention provides a security managing method for a medical image diagnostic apparatus that includes an operation terminal having an inputting device and a display device. The security managing method includes: a step of storing information on an area in which display shielding is activated; a step of detecting an event serving as a condition for activating the display shielding; and a step of reading, when the event is detected, the area information and creating display shielding screen information for causing the display device to display the display shielding on the basis of the area information read.

In order to attain the object, the invention provides a security managing method for a medical image diagnostic apparatus that includes an operation terminal having an inputting device and a display device. The security managing method includes: a step of storing shapes of a screen saver for respective execution states of an application; a step of detecting an event serving as an activation condition for the screen saver; a step of detecting an execution state of the application when the event serving as an activation condition for the screen saver is detected; and a step of creating screen saver image information for causing the display device to display the screen saver using a shape of the screen saver corresponding to the execution state of the application detected among the shapes of the screen saver stored.

According to a medical image diagnostic apparatus, a security managing system, and a security managing method according to the invention, it is possible to secure security of information by causing the operation terminal to display a display shielding screen to conceal information that is unsuitable for people other than a specific user to inspect and, on the other hand, cause the operation terminal to display desired information, which plural users desire to inspect, in a desired display method according to conditions such as a status of the apparatus and authorities of the respective users even while display shielding is active.

BRIEF DESCRIPTION OF THE DRAWINGS

FIG. 3 is a diagram showing an example of an operation screen that is displayed on a display device of an operation terminal when the status of the X-ray CT apparatus shown in FIG. 1 is an activation state shown in FIG. 2.

FIG. 4 is a diagram showing an example of an operation screen that is displayed on the display device of the operation terminal when the status of the X-ray CT apparatus shown in FIG. 1 is a patient registration state shown in FIG. 2.

FIG. 5 is a diagram showing an example of an operation screen that is displayed on the display device of the operation terminal when the status of the X-ray CT apparatus shown in FIG. 1 is an image photographing state shown in FIG. 2.

FIG. 6 is a diagram showing an example of an operation screen that is displayed on the display device of the operation terminal when the status of the X-ray CT apparatus shown in FIG. 1 is an image observation state shown in FIG. 2.

FIG. 12 is a diagram showing a third example of the screen saver screen shape information stored in the screen saver shape storing unit of the X-ray CT apparatus shown in FIG. 8.

FIG. 13 is a diagram showing a fourth example of the screen saver screen shape information stored in the screen saver shape storing unit of the X-ray CT apparatus shown in FIG. 8.

BEST MODE FOR CARRYING OUT THE INVENTION

Embodiments of a medical image diagnostic apparatus, a security managing system, and a security managing method according to the invention will be hereinafter explained.

The security managing system according to the invention is mounted on a general-purpose computer. In the following explanation, as an example, the security managing system is mounted on an operation terminal that is a computer constituting a part of a medical image diagnostic apparatus that is an example of a medical apparatus.

Figure 1:
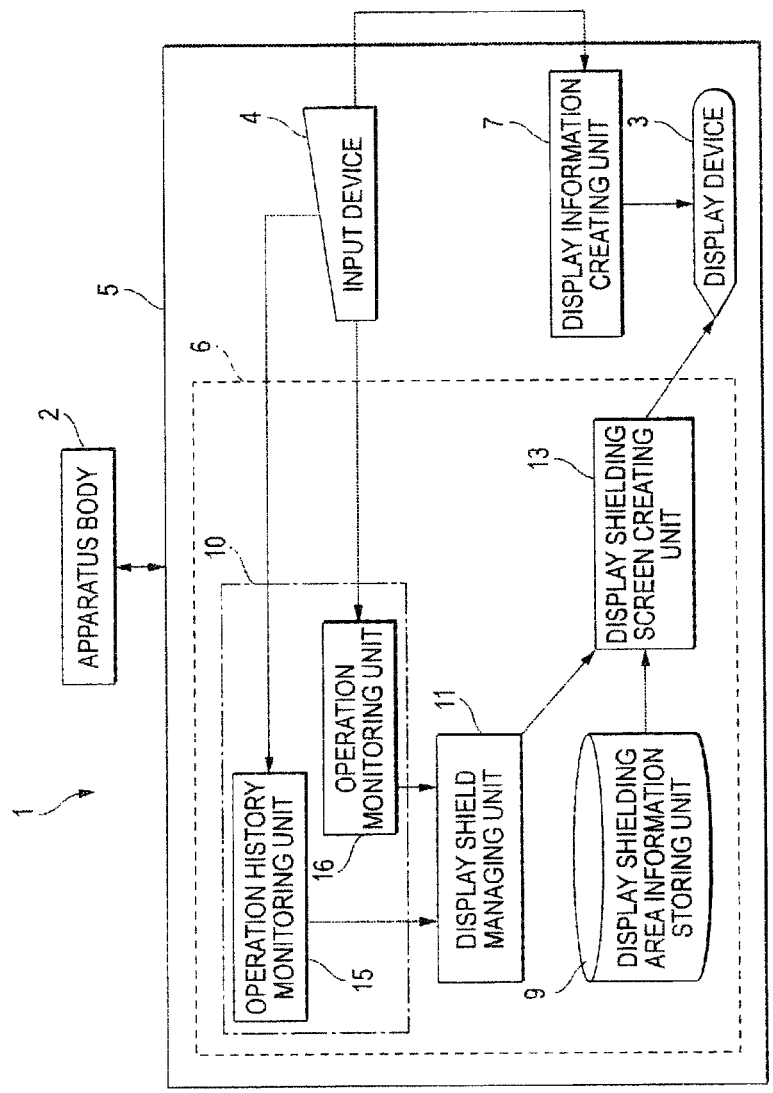
FIG. 1 is a diagram showing a first embodiment of a medical image diagnostic apparatus and a security managing system according to the invention.

FIG. 1 is a diagram showing a first embodiment of the medical image diagnostic apparatus and the security managing system according to the invention.

An X-ray CT apparatus 1 as an example of the medical image diagnostic apparatus includes an apparatus body 2 and an operation terminal 5 having a display device 3 and an input device 4. A security managing system 6 is mounted on the operation terminal 5. However, the security managing system 6 may be mounted on the apparatus body 2 or may be an independent external system. The medical image diagnostic apparatus may be an arbitrary medical image diagnostic apparatus such as an MRI (Magnetic resonance imaging) apparatus, an X-ray CT (Computed tomography) apparatus, an ultrasonic diagnostic apparatus, a PET (Positron emission computer tomography) apparatus, or an X-ray diagnostic apparatus. In this embodiment, the X-ray CT apparatus 1 will be explained as an example.

The X-ray CT apparatus 1 is operated according to information received from the input device 4 of the operation terminal 5 and can take statuses such as an activation state, patient registration, image photographing, image observation, and filing to be capable of transitioning from one status to another.

Figure 2:
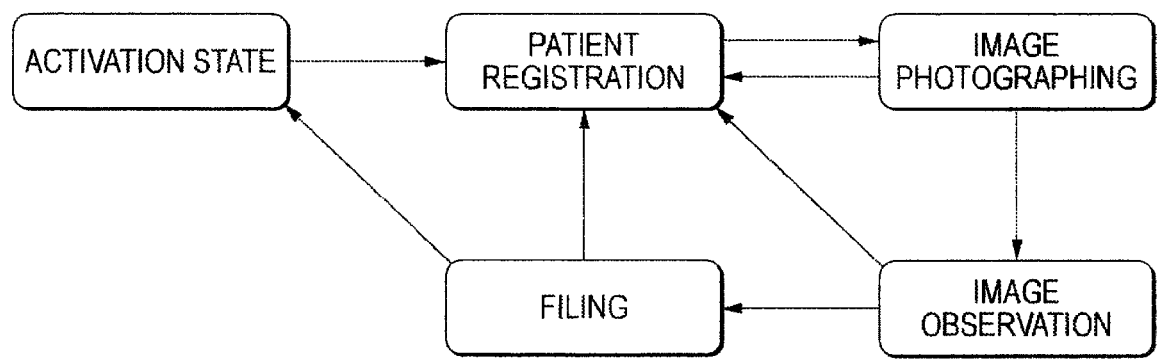
FIG. 2 is a transition chart of a status in an X-ray CT apparatus shown in FIG. 1.

FIG. 2 is a transition chart of the statues in the X-ray CT apparatus 1 shown in FIG. 1.

As shown in FIG. 2, it is possible to set the X-ray CT apparatus 1 in the activation state according to operation of the operation terminal 5. It is possible to transition the status from the activation state to the patient registration state, from the patient registration state to the image photographing state, from the image photographing state to the patient registration state or the image observation state, from the image observation state to the patient registration state or the filing state, and from the filing state to the patient registration state or the activation state, respectively. In the respective statuses, an operation screen is displayed on the display device 3 of the operation terminal 5.

FIG. 3 is a diagram showing an example of an operation screen that is displayed on the display device 3 of the operation terminal 5 when the status of the X-ray CT apparatus 1 shown in FIG. 1 is the activation state shown in FIG. 2.

As shown in FIG. 3, when the status of the X-ray CT apparatus 1 is the activation state, it is possible to input instructions such as new work, continued work, and end to the operation terminal 5 according to operation of the input device 4 with reference to the operation screen displayed on the display device 3. In other words, in the activation state, it is possible to select a type of processing by the X-ray CT apparatus 1.

In order to perform registration of patient information, a user can instruct start of patient registration processing according to operation of the input device 4 via the operation screen. Consequently, the status of the X-ray CT apparatus 1 transitions from the activation state to the patient registration state.

FIG. 4 is a diagram showing an example of an operation screen that is displayed on the display device 3 of the operation terminal 5 when the status of the X-ray CT apparatus 1 shown in FIG. 1 is the patient registration state shown in FIG. 2.

As shown in FIG. 4, when the status of the X-ray CT apparatus 1 is the patient registration state, a patient registration screen is displayed as an operation screen on the display device 3. It is possible to perform by operating the input device 4 with reference to the patient registration screen, registration of attribute information of a patient to be photographed and selection of a patient from a list of patients planned to be photographed. In this example of the patient registration screen, information such as personal information of a patient like a name and an age of the patient, activation buttons for other applications, and status information of the apparatus is displayed on the screen.

In this patient registration state, the user can perform input of patient information or, after selecting patient information from a patient list, perform instruction for start of image photographing by operating the input device 4 via the operation screen. Consequently, the status of the X-ray CT apparatus 1 transitions from the patient registration state to the image photographing state.

FIG. 5 is a diagram showing an example of an operation screen that is displayed on the display device 3 of the operation terminal 5 when the status of the X-ray CT apparatus 1 shown in FIG. 1 is the image photographing state shown in FIG. 2.

As shown in FIG. 5, when the status of the X-ray CT apparatus 1 is the image photographing state, an image photographing screen is displayed as an operation screen on the display device 3. It is possible to actually perform photographing of medical images by operating the input device 4 with reference to the image photographing screen. In this example of the image photographing screen, information such as attribute information of a patient to be photographed, a photographing progress state, an apparatus status, and activation buttons for other applications is displayed on the screen.

In this image photographing state, when the image photographing ends, the user can give an instruction for performing image observation to the X-ray Ct apparatus 1 according to operation of the input device 4 via the operation screen. Consequently, the status of the X-ray CT apparatus 1 transitions from the image photographing state to the image observation state.

FIG. 6 is a diagram showing an example of an operation screen that is displayed on the display device 3 of the operation terminal 5 when the status of the X-ray CT apparatus 1 shown in FIG. 1 is the image observation state shown in FIG. 2.

As shown in FIG. 6, when the status of the X-ray CT apparatus 1 is the image observation state, an image observation screen is displayed on the display device 3. It is possible to observe, with the image observation screen, a photographed image of a patient for whom photographing ends. In this example of the image observation screen, other than the image, attribute information of the image such as an ID (Identification) and a scan time, a progress state of image reconfiguration, activation buttons for other applications, and the like are displayed.

In this image observation state, at a point when the image observation by the user ends, it is possible to give an instruction for filing the image to the X-ray CT apparatus 1 according to operation of the input device 4. Consequently, the status of the X-ray CT apparatus 1 transitions form the image observation state to the filing state.

Figure 7:
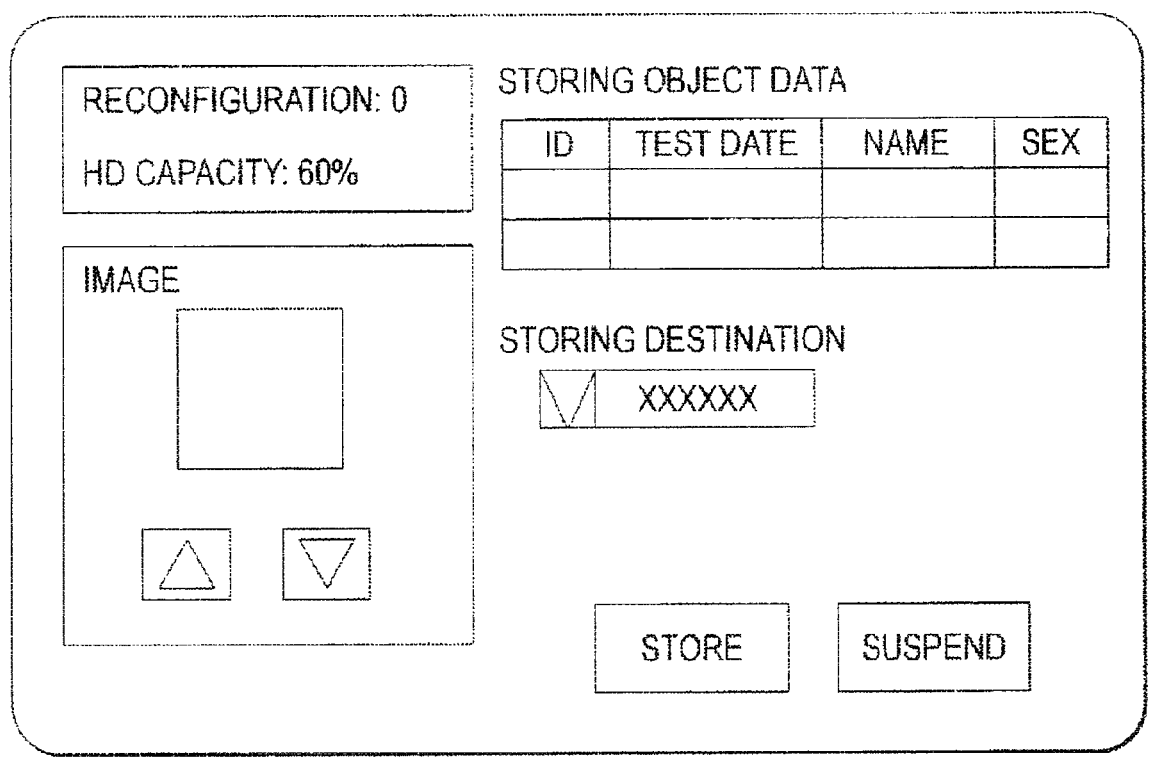
FIG. 7 is a diagram showing an example of an operation screen that is displayed on the display device of the operation terminal when the status of the X-ray CT apparatus shown in FIG. 1 is a filing state shown in FIG. 2.

FIG. 7 is a diagram showing an example of an operation screen that is displayed on the display device 3 of the operation terminal 5 when the status of the X-ray CT apparatus 1 shown in FIG. 1 is the filing state shown in FIG. 2.

As shown in FIG. 7, when the status of the X-ray CT apparatus 1 is the filing state, an image filing screen is displayed on the display device 3. It is possible to store a photographed image in a not-shown file server by operating the input device 4 with reference to the image filing screen. In this example of the image filing screen, information such as a section and an image for designating a storing destination and attribute information of storing object data is displayed.

In this way, not only in the X-ray CT apparatus 1 but also in various kinds of medical image diagnostic apparatuses, plural statuses are present and peculiar images corresponding to the statuses are displayed, respectively.

Therefore, a display information creating unit 7 for causing the display device 3 to display information corresponding to the respective statuses is provided in the operation terminal 5 of the X-ray CT apparatus 1. In other words, the display information creating unit 7 has a function of receiving information from the input device 4, creating image information for causing the display device 3 to display information corresponding to the respective statuses of the X-ray CT apparatus 1, and giving the image information to the display device 3.

The security managing system 6 includes a display shielding area information storing unit 9, a display shielding activation event detecting unit 10, a display shielding managing unit 11, and a display shielding screen creating unit 13.

It is possible to establish the display shielding area information storing unit 9, the display shielding activation event detecting unit 10, the display shielding managing unit 11, and the display shielding screen creating unit 13, which are components of the security managing system 6, by causing a computer to read a security managing program. However, a part or all of the components of the security managing system 6 may be constituted by circuits. The same holds true for the display information creating unit 7.

Information on an area in which display shielding is activated is stored in the display shielding area information storing unit 9 in advance. The area information for display shielding may be formed of screen data indicating information such as a start point, a shape (square, circle, ellipse, rhombus, parallelogram, etc.), and a size of a display shielding screen that should be displayed on the display device 3. Alternatively, the area information for display shielding may be indirect information for causing the display device 3 to display a display shielding screen such as a program for creating display shielding screen information.

The display shielding activation event detecting unit 10 includes an operation history monitoring unit 15 and an operation monitoring unit 16 in order to detect an event serving as an activation condition for display shielding.

The operation history monitoring unit 15 has a function of monitoring an operation history of the operation terminal 5 and detecting non-operation of the operation terminal 5 for a fixed time as an event serving as an activation condition for display shielding and a function of notifying the display shielding managing unit 11 of an indication that the event serving as an activation condition for display shielding is detected as an activation request for display shielding. In other words, the operation history monitoring unit 15 can measure an elapsed time from a final detection time of a key input event or a mouse operation event from the input device 4 such as a key or a mouse and, when the elapsed time exceeds a fixed time set in advance, detect that the operation terminal 5 is not operated.

The operation monitoring unit 16 has a function of monitoring operation of the operation terminal 5 and detecting performance of a series of key input operation set in advance by the input device 4 as an event serving as an activation condition or a cancellation condition for display shielding and a function of notifying the display shielding managing unit 11 of key input operation information indicting that the events are detected as an activation request for display shielding or a cancellation request for display shielding.

In other words, the operation monitoring unit 16 can acquire a key input event or a mouse operation event by the input device 4 and perform judgment on whether the key input event or the mouse operation event coincides with key operation or mouse operation defined in advance. Concerning the key input, input of one specific key may be set as an object of monitoring or simultaneous input of plural keys or sequential input of plural keys may be set as an object of monitoring. The key input operation information can be information that makes it possible to distinguish whether the information is an activation request for display shielding or a cancellation request for display shielding. However, rather than making the key input operation information distinguishable, the display shielding managing unit 11 may judge whether the key input operation information is an activation request for display shielding or a cancellation request for display shielding.

The display shielding managing unit 11 has a function of requesting, when an activation request for display shielding is received from the operation history monitoring unit 15 or the operation monitoring unit 16, the display shielding screen creating unit 13 to create and display a display shielding screen.

The display shielding managing unit 11 has a function of judging, when a series of key input operation information is received from the operation monitoring unit 16 as a cancellation request for display shielding, whether the key input operation information coincides with a cancellation condition for display shielding and a function of giving, when it is judged that the key input operation information coincides with the cancellation condition for display shielding, giving a non-display request for a display shielding screen to the display shielding screen creating unit 13. It is possible to provide, as required, in the display shielding managing unit 11, a function of causing the display device 3 to display an authentication screen by giving authentication screen information to the display device 3 and a function of performing authentication using the authentication information of the user received from the input device 4. It is possible to constitute the displaying shielding managing unit 11 to give a non-display request for a display shielding screen to the display shielding screen creating unit 13 only when the authentication is successful.

The display shielding screen creating unit 13 has a function of acquiring area information for display shielding, which should be displayed on the display device 3 as a display shielding screen from the display shielding area information storing unit 9 on the basis of a request for creation of a display shielding screen received from the display shielding managing unit 11 and a function of creating display shielding screen information on the basis of the display shielding area information acquired and giving the display shielding screen information to the display device 3 to thereby cause the display device 3 to display a display shielding screen.

Figure 8:
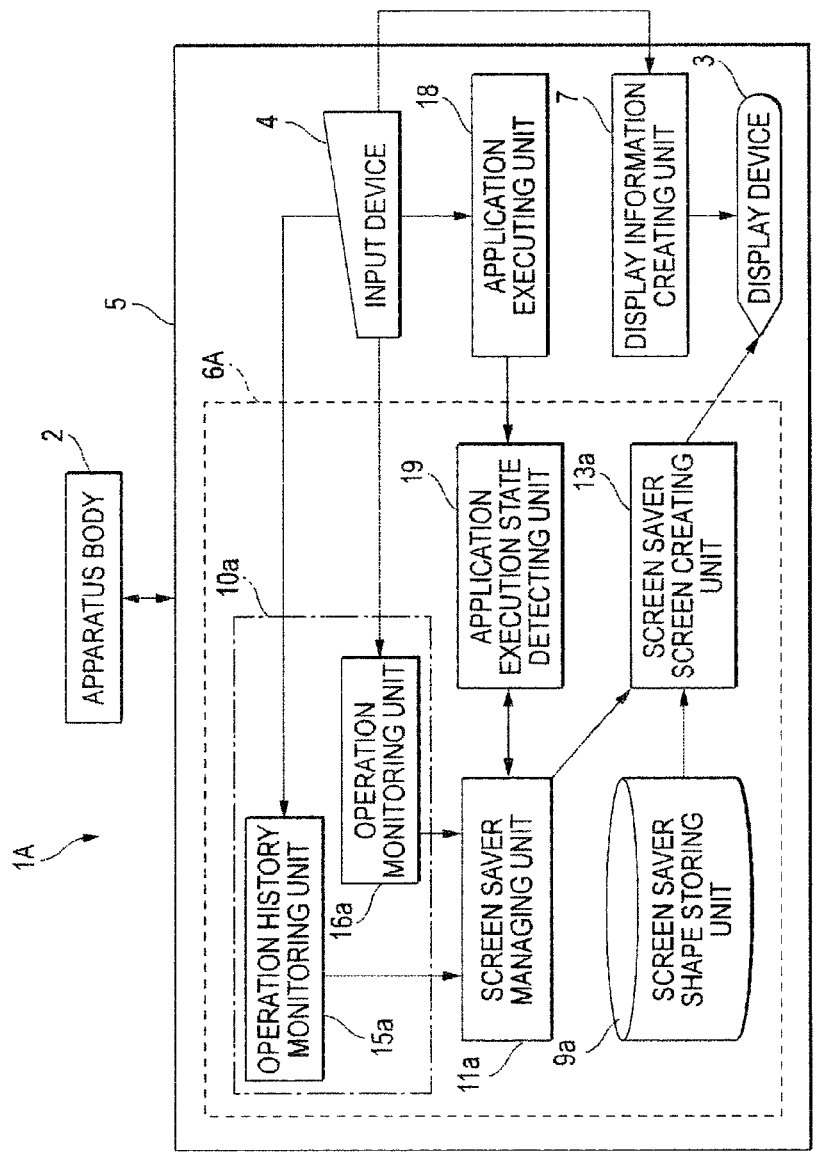
FIG. 8 is a diagram showing a specific example of the first embodiment of the medical image diagnostic apparatus and the security managing system.

FIG. 8 is a diagram showing a specific example of the first embodiment of the medical image diagnostic apparatus and the security managing system.

An X-ray CT apparatus 1A as an example of the medical image diagnostic apparatus includes the apparatus body 2 and the operation terminal 5 having the display device 3 and the input device 4. A security managing system 6A is mounted on the operation terminal 5. An application executing unit 18 is provided in the operation terminal 5 of the X-ray CT apparatus 1A. The application executing unit 18 has a function of executing various applications in the respective statuses in accordance with instructions received from the input device 4.

The operation terminal 5 includes a screen saver shape storing unit 9a as an example of the display shielding area information storing unit 9, a screen saver activation event detecting unit 10a as an example of the display shielding activation event detecting unit 10, as screen saver managing unit 11a as an example of the display shielding managing unit 11, and a screen saver screen creating unit 13a as an example of the display shielding screen creating unit 13. Moreover, the operation terminal 5 includes an application execution state detecting unit 19. The security managing system 6A is a system that performs security management for the X-ray CT apparatus 1A with the security managing method according to the invention. In the X-ray CT apparatus 1A shown in FIG. 8, components identical with those in the X-ray CT apparatus 1 shown in FIG. 1 are denoted by the identical reference numerals and signs. Explanations of the components are omitted.

It is possible to establish the screen saver shape storing unit 9a, the screen saver activation event detecting unit 10a, the screen saver managing unit 11a, the screen saver screen creating unit 13a, and the application execution state detecting unit 19, which are components of the security managing system 6A, by causing a computer to read a security managing program. However, a part or all of the components of the security managing system 6A may be constituted by circuits. The same holds true for the display information creating unit 7 and the application executing unit 18.

An operation history monitoring unit 15a of the screen saver activation event detecting unit 10a has a function of monitoring an operation history of the operation terminal 5 and detecting non-operation of the operation terminal 5 for a fixed time as an event serving as an activation condition for display shielding and a function of notifying the display shielding managing unit 11a of an indication that the event serving as an activation condition for display shielding is detected as an activation request for display shielding. In other words, the operation history monitoring unit 15a can measure an elapsed time from a final detection time of a key input event or a mouse operation event from the input device 4 such as a key or a mouse and, when the elapsed time exceeds a fixed time set in advance, detect that the operation terminal 5 is not operated.

An operation monitoring unit 16a has a function of monitoring operation of the operation terminal 5 and detecting performance of a series of key input operation set in advance by the input device 4 as an event serving as an activation condition or a cancellation condition for the screen saver and a function of notifying the screen saver managing unit 11a of key input operation information indicting that the events are detected as an activation request for the screen saver or a cancellation request for the screen saver.

In other words, the operation monitoring unit 16a can acquire a key input event or a mouse operation event by the input device 4 and perform judgment on whether the key input event or the mouse operation event coincides with key operation or mouse operation defined in advance. Concerning the key input, input of one specific key may be set as an object of monitoring or simultaneous input of plural keys or sequential input of plural keys may be set as an object of monitoring. The key input operation information can be information that makes it possible to distinguish whether the information is an activation request for the screen saver or a cancellation request for the screen saver. However, rather than making the key input operation information distinguishable, the screen saver managing unit 11a may judge whether the key input operation information is an activation request for the screen saver or a cancellation request for the screen saver.

The screen saver managing unit 11a has a function of requesting, when an activation request for the screen saver is received from the operation history monitoring unit 15a or the operation monitoring unit 16a, the application execution state detecting unit 19 to notify an execution state of an application and a function of receiving notification of the execution state of the application from the application execution state detecting unit 19 and requesting the screen saver screen creating unit 13a to create and display a screen saver screen. In this case, execution state information of the application, which is the notification of the execution state of the application, is included in the request for creation and display of the screen saver screen.

The screen saver managing unit 11a has a function of judging, when a series of key input operation information is received from the operation monitoring unit 16a as a cancellation request for the screen saver, whether the key input operation information coincides with a cancellation condition for the screen saver and a function of giving, when it is judged that the key input operation information coincides with the cancellation condition for the screen saver, a non-display request for a screen saver screen to the screen saver screen creating unit 13a. It is possible to provide, as required, in the screen saver managing unit 11a, a function of causing the display device 3 to display an authentication screen by giving authentication screen information to the display device 3 and a function of performing authentication using the authentication information of the user received from the input device 4. It is possible to constitute the screen saver managing unit 11a to give a non-display request for a screen saver screen to the screen saver screen creating unit 13a only when the authentication is successful.

The application execution state detecting unit 19 has a function of detecting, when a notification request for an execution state of an application is received from the screen saver managing unit 11a, an execution state of an application of the X-ray CT apparatus 1A at a point when the request is received from the screen saver managing unit 11a as application execution state information on the basis of application information under execution acquired from the application executing unit 18 and a function of notifying the screen saver managing unit 11a of the execution state of the application detected.

In this case, at least an execution status of the application is included in the execution state information of the application acquired by the application execution state detecting unit 19. Besides, it is possible to include arbitrary information such as user information indicating an attribute of the user using the application and a type of the application. The user information may be an identifier for uniquely identifying the user or may be role identifying information indicating a role of the user. The statuses of the X-ray CT apparatus 1A are not limited to the examples described above and can be defined in advance for each X-ray CT apparatus such that a type of a screen can be distinguished.

The screen saver screen creating unit 13a has a function of acquiring screen shape information (screen saver screen shape information) of a screen saver, which should be displayed on the display device 3 as a screen saver screen, from the screen saver shape storing unit 9a on the bases of application execution state information included the request for creation and display of a screen saver screen received from the screen saver managing unit 11a and a function of creating screen saver screen information on the basis of the screen saver screen shape information acquired and giving the screen saver screen information to the display device 3 to thereby cause the display device 3 to display the screen saver screen.

Screen saver screen shape information created for respective application execution states in advance is stored in the screen saver shape storing unit 9a. The screen saver screen shape information may be formed of screen data indicating information such as a start point, a shape (square, circle, ellipse, rhombus, parallelogram, etc.), and a size of a screen saver screen that should be displayed on the display device 3. Alternatively, the screen saver screen shape information may be indirect information for causing the display device 3 to display a screen saver screen such as a program for creating screen saver screen information.

Figures 9, 10, 11:
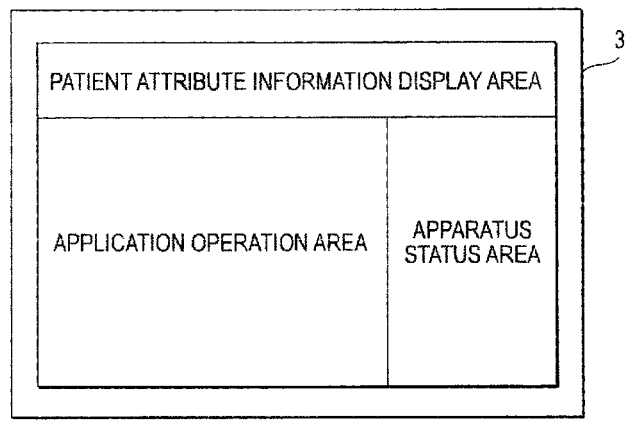
FIG. 9 is a diagram showing an example of an image photographing screen that is used as a base in creating screen saver screen shape information stored in a screen saver shape storing unit of an X-ray CT apparatus shown in FIG. 8.
FIG. 10 is a diagram showing a first example of the screen saver screen shape information stored in the screen saver shape storing unit of the X-ray CT apparatus shown in FIG. 8.
FIG. 11 is a diagram showing a second example of the screen saver screen shape information stored in the screen saver shape storing unit of the X-ray CT apparatus shown in FIG. 8.

FIG. 9 is a diagram showing an example of an image photographing screen that is used as a base in creating screen saver screen shape information stored in the screen saver shape storing unit 9a of the X-ray CT apparatus 1A shown in FIG. 8.

For example, in the following explanation, a shape of a screen saver screen applied to the image photographing screen shown in FIG. 9 is set. The image photographing screen shown in FIG. 9 is divided into a patient attribute information display area, an application operation area, and an apparatus status area. In this image photographing screen, when the patient attribute information display area and the application operation area are protected by a screen saver, a polygon obtained combining the patient attribute information display area and the application operation area is a screen shape of the screen saver.

Therefore, screen data of the polygon obtained by combining the patient attribute information display area and the application operation area of the image photographing screen is stored in the screen saver shape storing unit 9a as screen saver screen shape information in association with the application execution states. Examples of an execution state of an application (an execution status of an application) via the image photographing screen include execution states such as a patient registration state and an image photographing state.

FIG. 10 is a diagram showing a first example of the screen saver screen shape information stored in the screen saver shape storing unit 9a of the X-ray CT apparatus 1A shown in FIG. 8.

The screen saver screen shape information is formed by, for example, as shown in FIG. 10, associating an execution state of an application and screen data of a file format with each other. For example, when the execution state of the application is a state in which patient registration is performed, screen data of AAA.BMP is a screen shape of a screen saver.

FIG. 11 is a diagram showing a second example of the screen saver screen shape information stored in the screen saver shape storing unit 9a of the X-ray CT apparatus 1A shown in FIG. 8.

It is also possible to form the screen saver screen shape information by, for example, as shown in FIG. 11, adding not only execution content but also user information indicating an authority and an attribute of a user to the execution state of the application. For example, when the execution state of the application is a state in which an engineer performs patient registration, screen data of AA2.BMP is a screen shape of a screen saver.

FIG. 12 is a diagram showing a third example of the screen saver screen shape information stored in the screen saver shape storing unit 9a of the X-ray CT apparatus 1A shown in FIG. 8.

Moreover, it is also possible to form the screen saver screen shape information by, for example, as shown in FIG. 12, associating the execution state of the application and screen vertex data indicating vertexes of a polygon with each other. For example, when the execution state of the application is a state in which a doctor performs patient registration, an area of a polygon defined by screen vertex data (100,900) (100,0) (0,400) (400,500) (700,900) is a screen shape of a screen saver.

FIG. 13 is a diagram showing a forth example of the screen saver screen shape information stored in the screen saver shape storing unit 9a of the X-ray CT apparatus 1A shown in FIG. 8.

It is also possible to form the screen saver screen shape information by, for example, as shown in FIG. 13, associating display presence/absence information indicating whether area names specifying divided areas of a screen and respective areas are displayed (whether the areas are shielded by a screen saver) with the execution state of the application. In the example in FIG. 13, when the execution state of the application is a state in which a doctor performs patient registration, as a screen shape of a screen saver, the apparatus status area is displayed on the display device 3 and, on the other hand, the patient attribute information display area and the application operation area are not displayed. In this case, the respective areas are not limited to the areas such as the patient attribute information display area, the application operation area, and the apparatus status area shown in FIG. 9 and can be divided into arbitrary areas and defined.

In this way, it is possible to create the screen saver screen shape information in various format and store the screen saver screen shape information in the screen saver shape storing unit 9a. As shown in the examples in FIGS. 12 and 13, when the screen data itself defining a shape of a screen saver screen is not stored in the screen saver shape storing unit 9a, in the screen saver screen creating unit 13a, screen saver screen information is generated on the basis of the screen saver screen shape information.

Operations and processing of the X-ray CT apparatus 1A will be explained.

Figure 14:
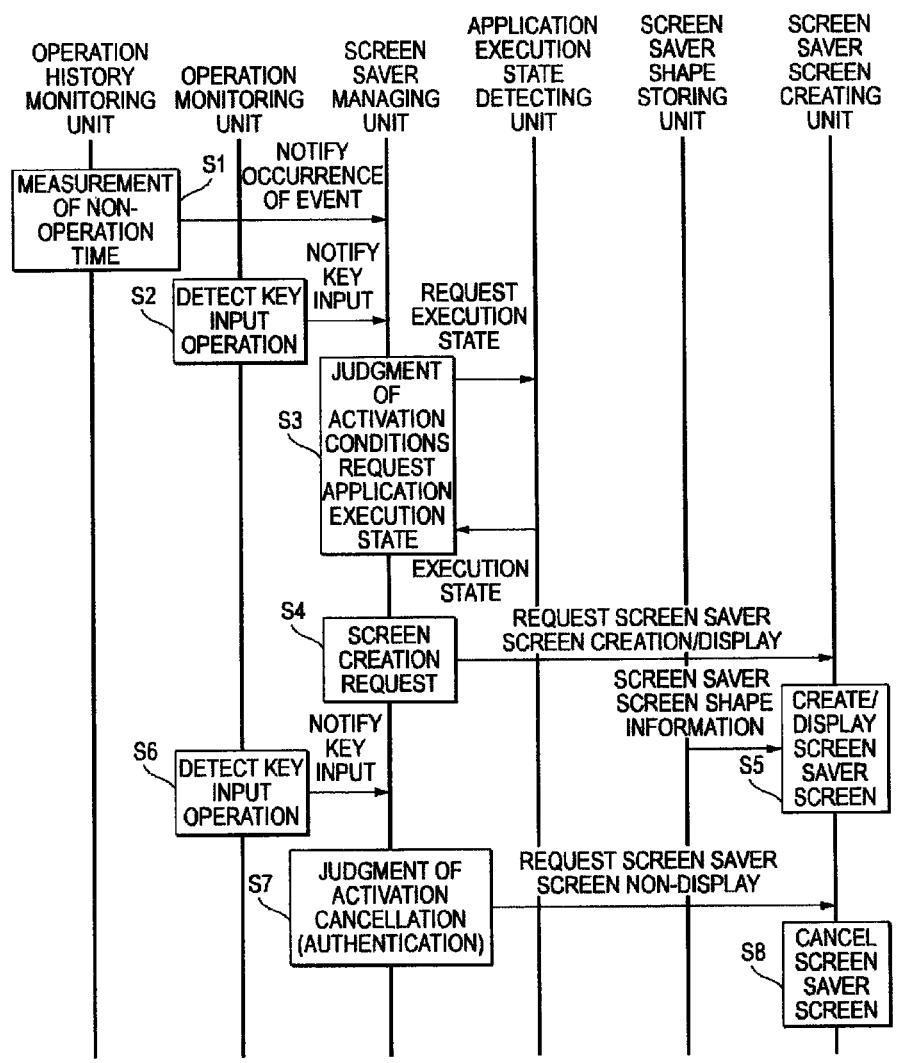
FIG. 14 is a sequence chart showing a flow in causing a display device to display a screen saver screen to perform security management for information in an operation terminal of the X-ray CT apparatus shown in FIG. 8.

FIG. 14 is a sequence chart showing a flow in causing the display device 3 to display a screen server screen and performing security management for information in the operation terminal 5 of the X-ray CT apparatus 1A shown in FIG. 8. In the figure, signs with numbers affixed to S denote respective steps of the sequence chart.

First, the X-ray CT apparatus 1A is activated to be in an arbitrary status in advance. Operation screens corresponding to the respective statuses shown in the examples in FIGS. 3 to 7 are displayed on the display device 3 provided in the operation terminal 5. An operation history of the operation terminal 5 is monitored by the operation history monitoring unit 15a and, in parallel, a key input event and a mouse operation event by the input device 4 is acquired by the operation monitoring unit 16a.

In this state, in step S1, for example, when key input or mouse operation by the input device 4 such as a key or a mouse is not performed for a fixed period, the operation history monitoring unit 15a detects that the operation terminal 5 is not operated. In other words, the operation history monitoring unit 15a measures an elapsed time 9a non-operation time) from time when last operation of the input device 4 such as key input or mouse operation is performed and, at a point when the elapsed time exceeds time set in advance, detects that the operation terminal 5 is not operated for the fixed period.

The operation history monitoring unit 15a gives a message for notifying occurrence of an event in that the operation terminal 5 is not operated for the fixed period to the screen saver managing unit 11a as an activation request for a screen saver.

On the other hand, in step S2, when fixed key input or fixed mouse operation for screen saver activation defined in advance is performed, it is detected by the operation monitoring unit 16a, which monitors specific key input, that a series of key input operation is performed. The operation monitoring unit 16a notifies the screen saver managing unit 11a of a message indicating that the series of key input operation is performed by the operation terminal 5 as an activation request for the screen saver.

In other words, at a point when an event set in advance in monitoring objects occurs, the operation history monitoring unit 15a and the operation monitoring unit 16a notifies the screen saver managing unit 11a of an activation request for the screen saver. At this point, when the fixed key input or the fixed mouse operation for screen saver activation is performed, a type of an inputted key in included in the notification of the activation request for the screen saver to the screen saver managing unit 11a as required.

In step S3, the screen saver managing unit 11a receives the screen saver activation request, the screen saver managing unit 11a judges whether activation conditions for the screen saver are satisfied. When the activation conditions are satisfied, in order to start activation of the screen saver, the screen saver managing unit 11a requests the application execution state detecting unit 19 to notify an execution state of an application in the X-ray CT apparatus 1A. Therefore, the application execution state detecting unit 19 detects an execution state of an application of the X-ray CT apparatus 1A at a point when the request from the screen saver managing unit 11a is received on the basis of information on an application under execution acquired from the application executing unit 18.

As the detection of an execution state of an application, every time the application executing unit 18 executes each application, information on the application under execution is notified from the application executing unit 18 to the application execution state detecting unit 19 in advance such that the application execution state detecting unit 19 can store latest information on an application under execution while updating the information. However, at a point when the application execution state detecting unit 19 receives a notification request for an execution state of an application from the screen saver managing unit 11a, the application execution state detecting unit 19 can also inquire of the application executing unit 18 about an application under execution.

In step S4, the screen saver managing unit 11a request the screen saver screen creating unit 13a to create and display a screen saver screen. Information on an execution state of an application including a status of the X-ray CT apparatus 1A and user information given to the screen saver managing unit 11a from the application execution state detecting unit 19 is included in the request for creation and display of a screen saver screen.

In step S5, the screen saver screen creating unit 13a acquires screen saver screen shape information, which should be displayed on the display device 3 as a screen saver screen, from the screen saver shape storing unit 9a on the basis of the application execution state information included in the request for creation and display of a screen saver screen received from the screen saver managing unit 11a. The screen saver screen creating unit 13a creates screen saver screen information on the basis of the screen saver screen shape information acquired from the screen saver shape storing unit 9a and gives the screen saver screen information to the display device 3. Consequently, a screen saver screen created by the screen saver screen creating unit 13a is displayed on the display device 3 and the activation of a screen saver is completed.

The screen saver screen displayed on the display device 3 assumes a shape corresponding to an attribute and an authority of a user for each of execution states of applications in the respective statuses. Thus, it is possible to secure security of information by selectively concealing only information, which is unsuitable for people other than a specific user to inspect, according to a user and an execution state of an application. Moreover, it is possible to cause the display device 3 of the operation terminal 5 to display desired information, which plural users desire to inspect, in a desired display method according to conditions such as an execution state of an application and authorities of the respective users even while display shielding is active.

In order to cancel activation of the screen saver, the user operates the input device 4 of the operation terminal 5.

Therefore, in step S6, key input monitoring for the input device 4 is performed by the operation monitoring unit 16a. The operation monitoring unit 16a detects that some operation such as input of an arbitrary key or key input or mouse operation decided in advance of the input device 4 is performed. The operation monitoring unit 16a notifies the screen saver managing unit 11a of a series of key input operation information indicating that a series of key input operation is performed.

In step S7, since the screen saver is in the activated state, the screen saver managing unit 11a interprets the key input operation information received from the operation monitoring unit 16a as a cancellation request for the screen saver and judges whether the key input operation information coincides with cancellation conditions for the screen saver. When it is judged that the key input operation information coincides with the cancellation conditions for the screen saver, the screen saver managing unit 11a gives authentication screen information for canceling activation of the screen saver to the display device 3.

Therefore, an authentication screen for canceling activation of the screen saver is displayed on the display device 3. The user can instruct cancellation of the screen saver by inputting an ID and a password from the input device 4 via the authentication screen. In this case, it is desirable to limit a user who can instruct cancellation of the screen saver to only a user who is logging in the X-ray CT apparatus 1A. However, the user who can instruct cancellation of the screen saver is not limited to this. For example, a cancellation authority for the screen saver may be given to users belonging to the same authority group as the user or may be given to only an administrator other than the user.

The screen saver managing unit 11a receives authentication information of the user inputted to the input device 4 and performs authentication. When the authentication is successful, the screen saver managing unit 11a gives a non-display request for a screen saver screen to the screen saver screen creating unit 13a.

In step S7, the screen saver screen creating unit 13a cancels the screen saver displayed on the display device 3 in accordance with the non-display request for the screen saver screen received from the screen saver managing unit 11a. The user can use a desired application according to operation of the input device 4 with reference to the display device 3 of the operation terminal 5.

The application executing unit 18 may execute applications of the respective statutes and display pieces of information of the respective statuses on the display device 3 while superimposing the pieces of information one on top of another. In that case, in step S3, in order to start activation of a screen saver, the screen saver managing unit 11a requests the application execution state detecting unit 19 to notify an execution state of an application executed lately. Therefore, the application execution state detecting unit 19 detects a latest execution state of an application on the basis of the information on the application under execution acquired from the application executing unit 18.

Figure 15:
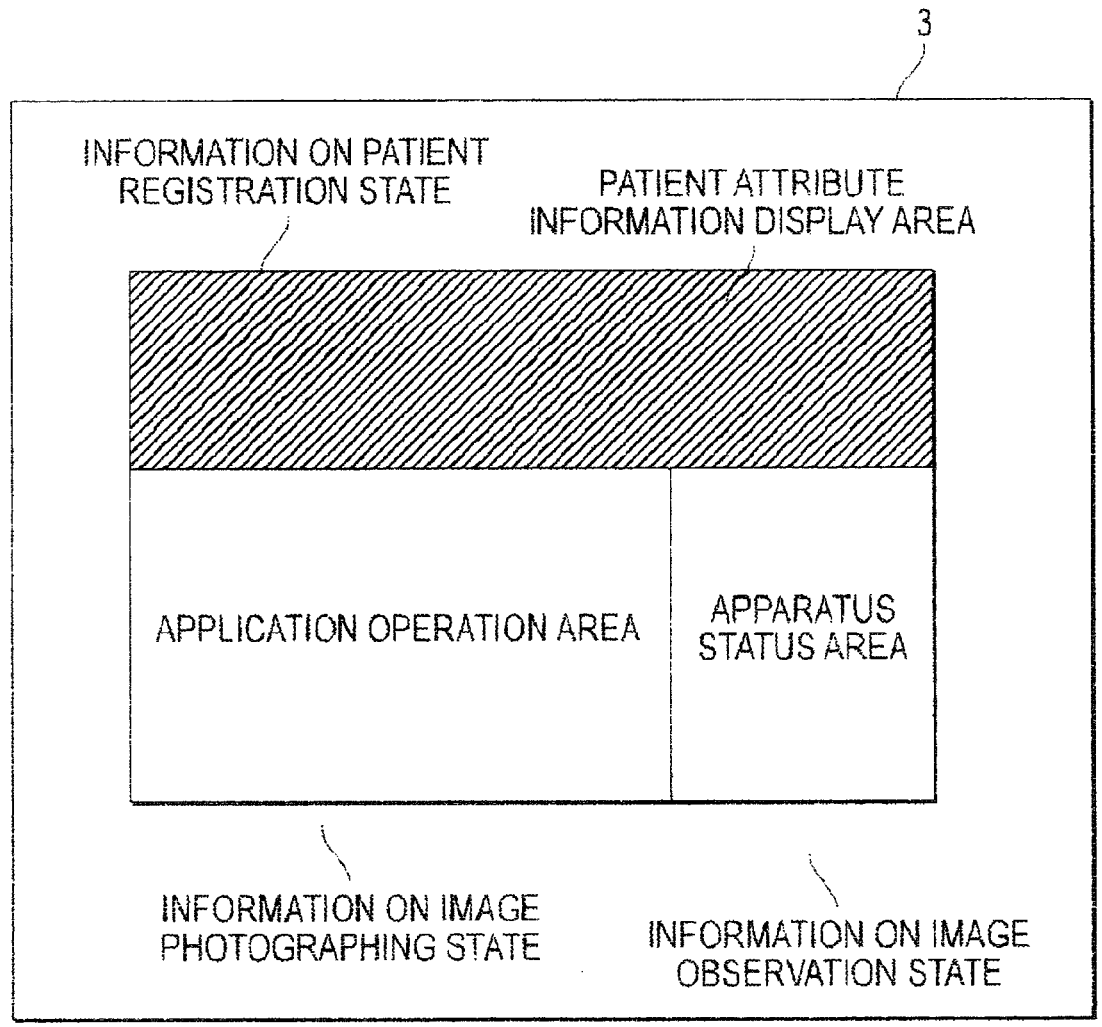
FIG. 15 is a diagram showing an example of a screen saver screen at the time when respective pieces of information on statuses are displayed on the display device while being superimposed one on top of another.

FIG. 15 is a diagram showing an example of a screen saver screen at the time when respective pieces of information on respective statuses are displayed on the display device 3 while being superimposed one on top of another.

FIG. 15 shows a screen saver screen at the time when applications of respective statuses, for example, the patient registration state, the image photographing state, and the image observation state shown in FIG. 2 are executed, respectively, and pieces of the respective statuses are displayed on the display device 3 while being superimposed one on top of another. When the application of the patient registration state is performed lately, in step S5, the screen saver screen creating unit 13a acquires screen saver screen shape information, which should be displayed on the display device 3 as a screen saver screen, from the screen saver shape storing unit 9a on the basis of information on the patient registration state included in the request for creation and display of the screen saver screen received from the screen saver managing unit 11a. The screen saver screen creating unit 13a creates screen saver screen information on the basis of the screen saver screen shape information acquired from the the screen saver screen shape information acquired from the screen saver shape storing unit 9a and gives the screen saver screen information to the display device 3.

Thus, it is possible to secure security of information by selectively concealing only information, which is unsuitable for people other than a specific user to inspect, among information on the patient registration state displayed in the front of the display device 3 according to a user and an execution state of an application. In FIG. 15, it is assumed that only the patient attribute information display area among the information on the patient registration state is concealed. Even in information on the image photographing state and information on the image observation state that are displayed in the rear of the information on the patient registration state, areas thereof not covered by the information on the patient registration information displayed in the front may be concealed.

According to the X-ray CT apparatus 1 and the security managing system 6 described above, it is possible to display a display shielding screen according to desired area information. Therefore, it is possible to display the display shielding screen in the same color and arrangement as a screen used by the user in his/her daily work.

According to the X-ray CT apparatus 1A and the security managing system 6A, it is possible to display a screen saver screen of a desired shape according to a status or an execution state of an application. Moreover, it is possible to display a screen saver screen in a desired shape according to not only the status but also a user who uses the application. Therefore, it is possible to display the display shielding screen in the same color and arrangement as a screen used by the user in his/her daily work.

As a result, it is possible to secure security of information by selectively and changeably concealing information displayed on the display device 3 according to conditions of use and, on the other hand, display desired information that the user desires to inspect.

Figure 16:
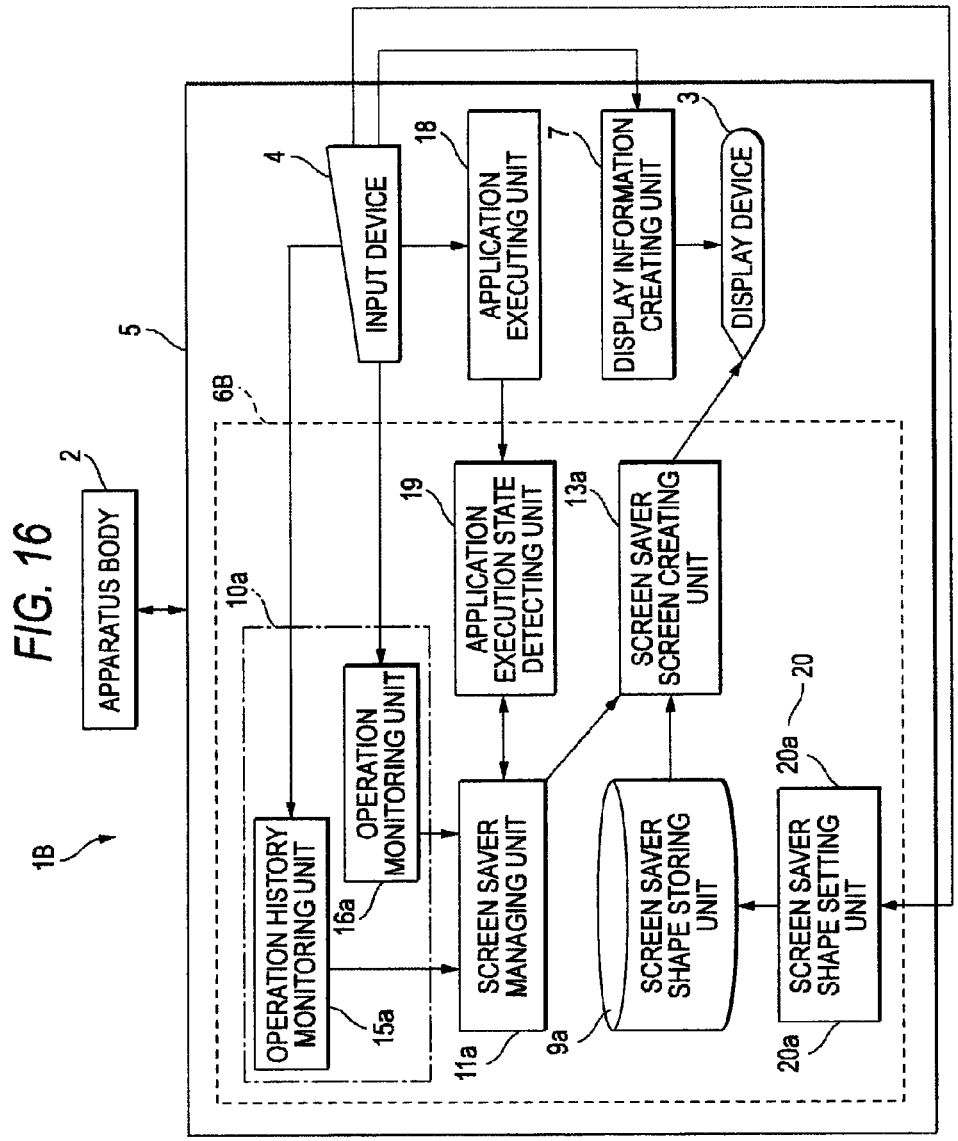
FIG. 16 is a diagram showing a second embodiment of the medical image diagnostic apparatus and the security managing system according to the invention.

FIG. 16 is a diagram showing a second embodiment of the medical image diagnostic apparatus and the security managing system according to the invention.

An X-ray CT apparatus 1B as an example of the medical image diagnostic apparatus shown in FIG. 16 is different from the X-ray CT apparatus 1A shown in FIG. 8 in that a screen saver shape setting unit 20a is provided in the security managing system. The other constitutions and actions are not substantially different from those of the X-ray CT apparatus 1A shown in FIG. 8. Thus, components same as those of the X-ray CT apparatus 1A are denoted by the same reference numerals and signs. Explanations of the components are omitted.

In a security managing system 6B of the X-ray CT apparatus 1B, the screen saver shape setting unit 20a as an example of the display shielding information setting unit 20 that sets area information of display shielding is provided. The screen saver shape setting unit 20a has a function of receiving input from the input device 4 and creating screen saver screen shape information by associating an application execution state and a screen shape of a screen saver and a function of storing the screen saver screen shape information created in the screen saver shape storing unit 9a by writing the screen saver screen shape information therein.

In this case, the screen saver shape setting unit 20a is constituted to be capable of causing the display device 3 to display an operation screen necessary for creating screen saver screen shape information.

Figure 17:
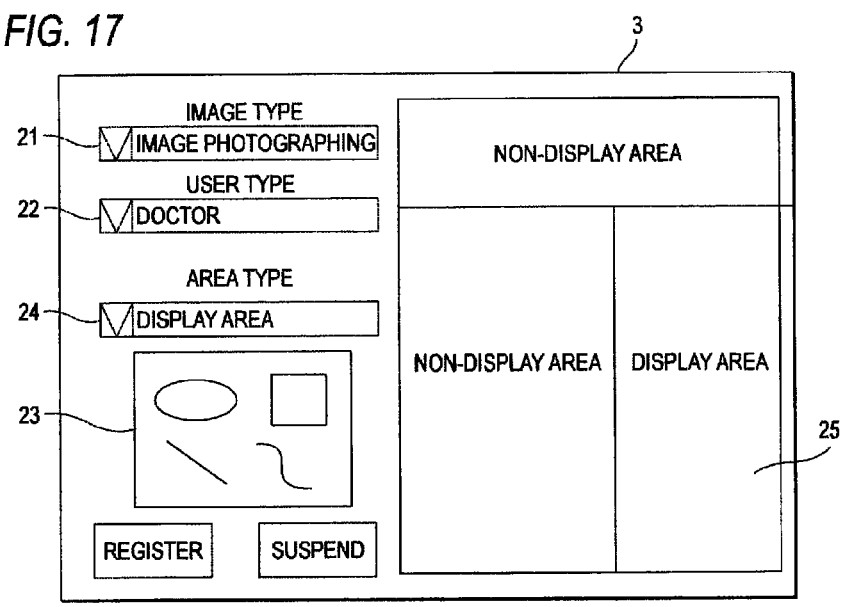
FIG. 17 is a diagram showing an example of a screen for creation of screen saver screen shape information displayed as an operation screen on a display device of an X-ray CT apparatus shown in FIG. 16.

FIG. 17 is a diagram showing an example of a screen for creating screen saver screen shape information that is displayed as an operation screen on the display device 3 of the X-ray CT apparatus 1B shown in FIG. 16.

Screen information for creating screen saver screen shape information is given to the display device 3 from the screen saver shape setting unit 20a. For example, a screen for creating screen saver screen shape information shown in FIG. 17 is displayed on the display device 3.

In the screen for creating screen saver screen shape information, for example, a screen type section 21 for selecting a type of a screen to be displayed on a screen saver screen, a user type section 22 for selecting a type of a user, an area designation pallet 23 for using a tool for defining an area, an area type section 24 for designating an area type for designating whether an area defined at the time of activation of a screen saver is displayed or not displayed, and a sample image display area 25 for displaying a sample image of a screen saver screen.

When the user selects a screen type such as an image photographing screen and a user type such as a doctor according to operation of the input device 4, a sample image of a screen corresponding to an attribute of the user is displayed in the sample image display area 25. Then, the user can define an area on the sample image using rendering tools such as figures and lines provided in the area designation pallet 23. Subsequently, in the area type section 24, the user designates a display attribute of an area indicating whether the area defined is an area that should be displayed or an area that should not be displayed. In other words, the user sets an area, which the user desires to display at the time of activation of the screen saver, as a display area.

When a shape of a screen saver is determined in this way, it is possible to create screen saver screen shape information including the shape determined and cause the screen saver shape storing unit 9a to store the screen saver screen shape information. When screen saver screen shape information is created via the screen for creating screen saver screen shape information shown in FIG. 17, screen saver screen shape information is stored in the screen saver shape storing unit 9a in the formats shown in FIGS. 10 to 12.

Figure 18:
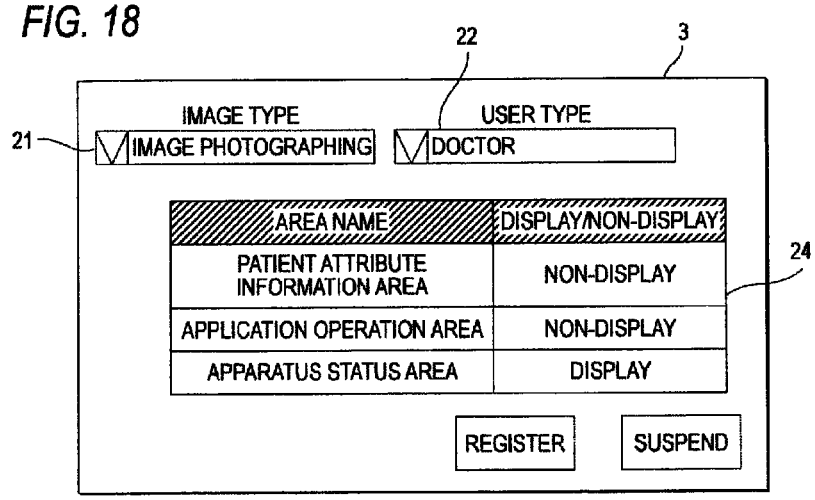
FIG. 18 is a diagram showing another example of the screen for creation of screen saver screen shape information displayed as the operation screen on the display device of the X-ray CT apparatus shown in FIG. 16.

FIG. 18 is a diagram showing another example of the screen for creating screen saver screen shape information that is displayed as an operation screen on the display device 3 of the X-ray CT apparatus 1B shown in FIG. 16.

It is also possible to display, for example, the screen for creating screen saver screen shape information shown in FIG. 18 on the display device 3.

In the screen for creating screen saver screen shape information, for example, an area type section 24 for designating whether plural areas divided in advance are displayed or not displayed is provided other than the screen type section 21 for selecting a type of a screen to be displayed on a screen saver screen and the user type section 22 for selecting a type of a user.

When the user selects a screen type such as an image photographing screen and a user type such as doctor according to operation of the input device 4, the area type section 24 for designating whether plural areas divided in advance are displayed or not displayed is displayed, for example, in an ideographic format on a screen corresponding to an attribute of the user. For example, when the screen type is image photographing and the user type is a doctor, area names are a patient attribute information display area, an application operation area, and an apparatus status area. Then, the user can perform setting for displaying or not displaying the respective areas in the area type section 24 displayed in the ideographic format.

When a shape of a screen saver is determined in this way, it is possible to create screen saver screen shape information including the shape determined and cause the screen saver shape storing unit 9a to store the screen saver screen shape information. When the screen saver screen shape information is created via the screen for creating screen saver screen shape information shown in FIG. 18, the screen saver screen shape information is stored in the screen saver shape storing unit 9a in the format shown in FIG. 13.

In other words, the X-ray CT apparatus 1B and the security managing system 6B described above allow a user to create screen saver screen shape information with desired contents. Therefore, according to the X-ray CT apparatus 1B and the security managing system 6B, in addition to the same effects as the X-ray CT apparatus 1A shown in FIG. 8, respective users can set a shape of a screen saver in desired shapes according to roles and authorities of the users. Thus, it is possible to improve convenience for the users. In particular, as shown in FIG. 18, if a user performs setting only for whether an area set for each screen in advance is displayed or not displayed, it is possible to more easily create screen saver screen shape information.

Figure 19:
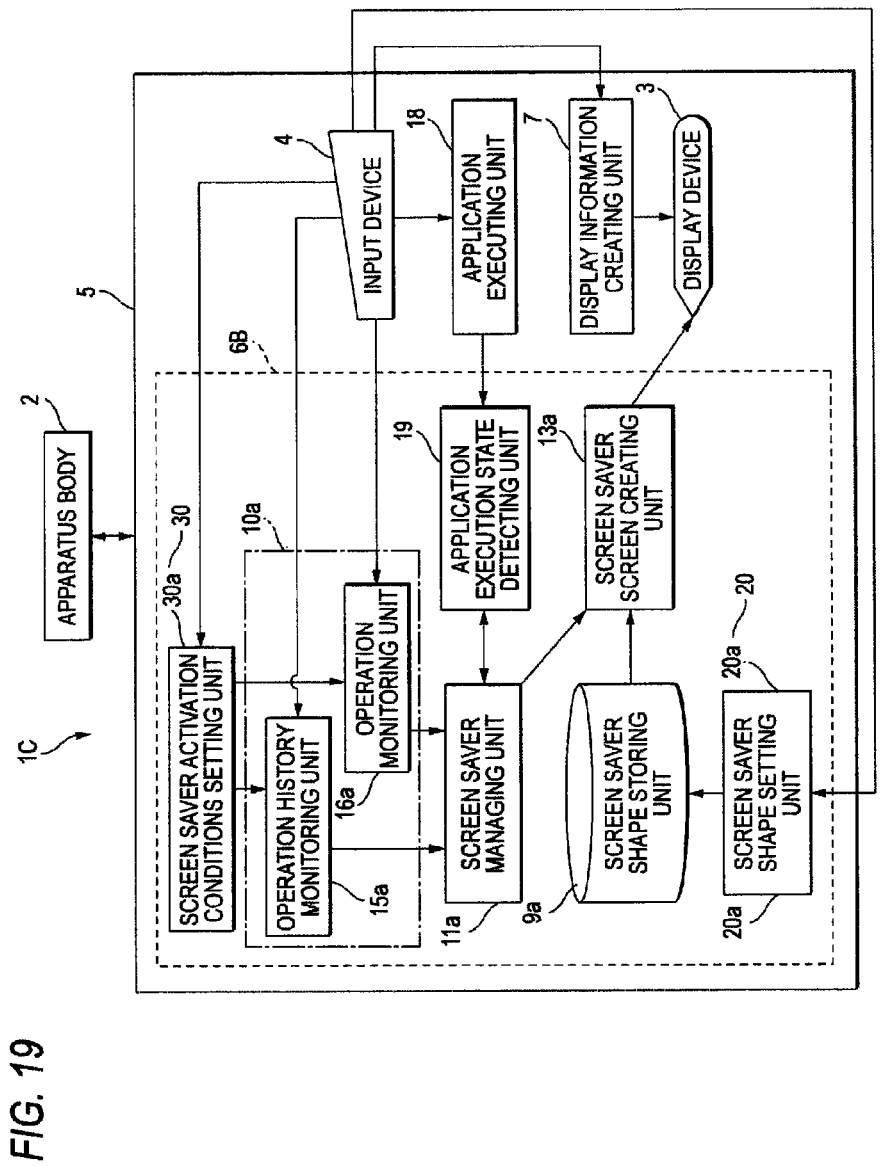
FIG. 19 is a diagram showing a third embodiment of the medical image diagnostic apparatus and the security managing system according to the invention.

FIG. 19 is a diagram showing a third embodiment of the medical image diagnostic apparatus and the security managing system according to the invention.

An X-ray CT apparatus 1C as an example of the medical image diagnostic apparatus shown in FIG. 19 is different from the X-ray CT apparatus 1B shown in FIG. 16 in that a screen saver activation conditions setting unit 30a is provided in the security managing system. The other constitutions and actions are not substantially different from those of the X-ray CT apparatus 1B shown in FIG. 16. Thus, components identical with those in the X-ray CT apparatus 1B are denoted by the same reference numerals and signs. Explanations of the components are omitted.

In other words, the screen saver activation conditions setting unit 30a as an example of a display shielding activation conditions setting unit 30 that sets activation conditions for display shielding is provided in the security managing system 6C of the X-ray CT apparatus 1C. The screen saver activation conditions setting unit 30a has a function of receiving input from the input device 4, setting activation conditions and cancellation conditions for a screen saver, and giving the activation conditions and the cancellation conditions to one or both of the operation history monitoring unit 15a and the operation monitoring unit 16a.

As the activation conditions for the screen saver, it is possible to set a condition concerning whether an elapsed time from the last operation by the input device 4 exceeds a fixed time or whether a specific series of key input is performed. As the cancellation conditions for the screen saver, other than key operation for canceling the screen saver by the input device 4, it is possible to designate authentication conditions on an authentication screen displayed by key operation for canceling the screen saver. As the authentication conditions in canceling the screen saver, it is preferable if it is possible to designate authentication conditions that, for example, a user is identical with a user who has logged in and is a user or an administrator having an identical authority.

The screen saver activation conditions setting unit 30a is constituted to be capable of causing the display device 3 to display a setting screen necessary for setting activation conditions and cancellation conditions for a screen saver by giving image information to the display device 3.

Figure 20:
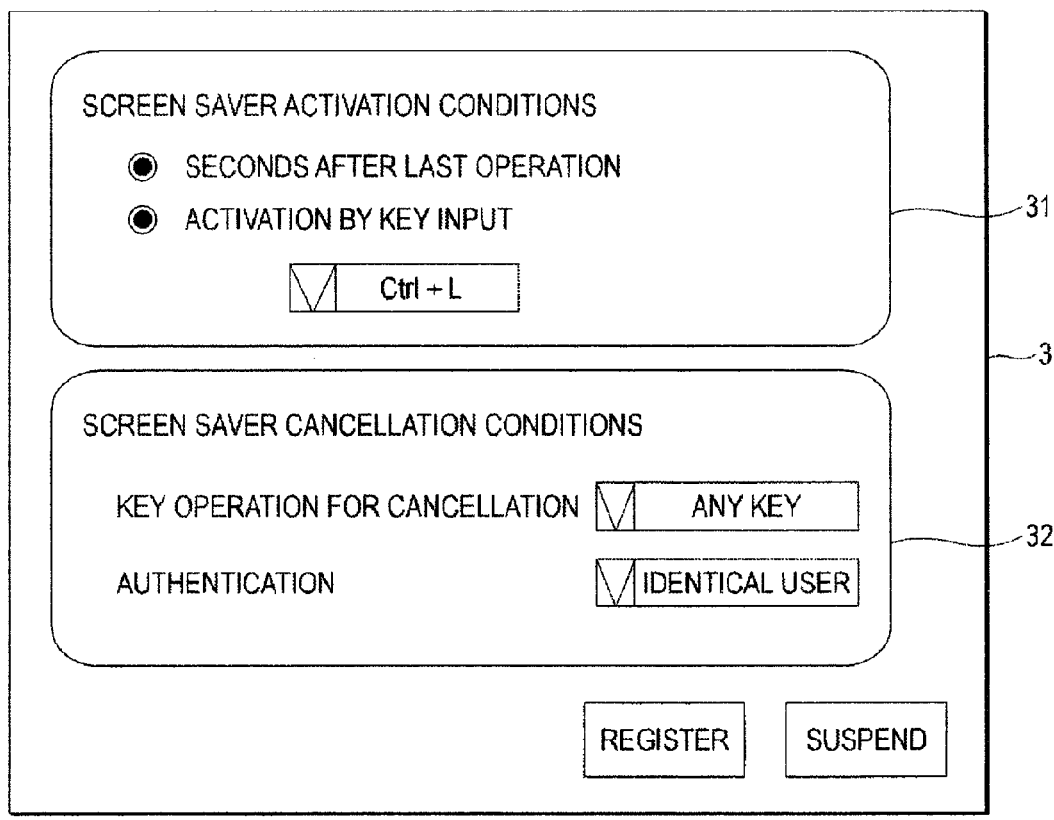
FIG. 20 is a diagram showing an example of a setting screen for setting activation conditions and cancellation conditions for a screen saver displayed on a display device of an X-ray CT apparatus shown in FIG. 19.

FIG. 20 is a diagram showing an example of a setting screen for setting activation conditions and cancellation conditions for a screen saver that is displayed on the display device 3 of the X-ray CT apparatus 1C shown in FIG. 19.

As shown in FIG. 20, an activation conditions setting section 31 for setting activation conditions for a screen saver and a cancellation conditions setting section 32 for setting cancellation conditions for a screen saver are provided in the setting screen. In the activation conditions setting section 31 for setting activation conditions for a screen saver, it is possible to perform designation of a no-operation time until screen saver activation and designation of key operation and mouse operation in activating the screen saver with key input. In the cancellation conditions setting section 32 for setting cancellation conditions for a screen saver, it is possible to designate key operation or mouse operation in canceling the screen saver and designate an attribute of a user at the time of authentication.

In other words, the X-ray CT apparatus 1C and the security managing system 6C described above allow a user to arbitrarily set activation conditions and cancellation conditions for a screen saver. Therefore, according to the X-ray CT apparatus 1C and the security managing system 6C, in addition to the same effects as the X-ray CT apparatus 1B shown in FIG. 16, respective users can set activation conditions and cancellation conditions for a screen saver to be desired conditions. Thus, it is possible to improve convenience for the users. In particular, it is possible to set activation conditions and cancellation conditions for a screen saver in association with an attribute of a user and a screen. In this way, it is possible to further improve convenience for the user and perform careful security management.

In the X-ray CT apparatuses 1, 1A, 1B, and 1C and the security managing systems 6, 6A, 6B, and 6C in the respective embodiments, a part of the functions and processing do not have to be provided. It is also possible to include, other than a role and an authority of a user, arbitrary information such as a patient attribute of image data forming a screen, an attribute of a user who has photogrpahed image data, an attribute of a test, and an attribute of an X-ray CT apparatus in the screen saver screen shape information. In this case, if the user can associate pieces of information by selecting the information from an item list, it is possible to improve convenience.

The invention claimed is:

1. A medical image diagnostic apparatus that includes an operation terminal having an input device and a display device, which is configured to shift a step-by-step process status having a plurality of process application execution states from one state to another, the states including an image photographing process application execution state, a patient registration process application execution state, an image observation process application execution state, and a filing process application execution state, the medical image diagnostic apparatus comprising:
   a display shielding area storing unit configured to store display shielding areas of the respective states, which are within a screen of the display device for each of the application execution states, in which display shielding is activated;
   an event detecting unit configured to detect an event not to use the operation terminal for a fixed time;
   a process application execution state detecting unit configured to detect a process application execution state of the operation terminal; and
   a display shielding image generating unit configured to read, when the event is detected by the event detecting unit, data of a display shielding area from the display shielding area storing unit, corresponding to the detected state and to generate data of a display shielding image for shielding the read display shielding area.

2. The medical image diagnostic apparatus according to claim 1, wherein
   attribute information of a patient to be photographed, a photographing progress situation, an apparatus status, and activation buttons for other process applications is displayed on the screen under the image photographing process application execution state.

3. A medical image diagnostic apparatus that includes an operation terminal having an input device and a display device, which is configured to shift a step-by-step process status having a plurality of process application execution states from one state to another, the states including an image photographing process application execution state, a patient registration process application execution state, an image observation process application execution state, and a filing process application execution state, the medical image diagnostic apparatus comprising:

a part-screen saver shape storing unit configured to store part-screen saver image shapes of the respective states, wherein each part-screen saver image shape is to shield a part of a screen of the display device;

an event detecting unit configured to detect an event not to use the operation terminal for a fixed time;

a process application execution state detecting unit configured to detect a process application execution state of the operation terminal;

a part-screen saver managing unit configured to perform, when the event is detected by the event detecting unit, a generation requirement of the part-screen saver with the detected state; and a part-screen saver image generating unit configured to read data of a screen saver image shape from the part-screen saver shape storing unit, corresponding to the detected state based on the generation requirement, and to generate data of a part-screen saver image for shielding the read screen saver image shape.

4. The medical image diagnostic apparatus according to claim 3, further comprising:

a part-screen saver shape setting unit configured to give data of an operation image to the display device to cause the screen to display the operation image to set the part-screen saver image shape based on information received from the input device and to write the set part-screen saver image shape into the part-screen saver storing unit to cause the part-screen saver storing unit to store the set part-screen saver image shape.

5. The medical image diagnostic apparatus according to claim 3, further comprising:

a fixed time setting unit configured to give data of an operation image to the display device to cause the screen to display the operation image and to set the fixed time based on information received from the input device, wherein the event detecting unit detects the event base on the fixed time received from the fixed time setting unit.

6. The medical image diagnostic apparatus according to claim 3, wherein the process application execution state detecting unit detects a type of an activated application and an execution status of the activated application as well as the state.

7. The medical image diagnostic apparatus according to claim 3, wherein the process application execution state detecting unit detects an attribute of a user of an activated application and an execution status of the activated application as well as the state.

8. The medical image diagnostic apparatus according to claim 3, wherein attribute information of a patient to be photographed, a photographing progress situation, an apparatus status, and activation buttons for other process applications is displayed on the screen under the image photographing process application execution state.

9. A security managing system that includes an operation terminal having an input device and a display device, which is able to shift a step-by-step process status having a plurality of process application execution states, from one state to another, the states including an image photographing process application execution state, a patient registration process application execution state, an image observation process application execution state, and a filing process application execution state, the security managing system comprising:

a display shielding area storing unit configured to store display shielding areas of the respective states, which are within a screen of the display device, in which display shielding is activated;

an event detecting unit configured to detect an event not to use the operation terminal for a fixed time;

a process application execution state detecting unit configured to detect a process application execution state of the operation terminal; and a display shielding image generating unit configured to read, when the event is detected by the event detecting unit, data of a display shielding area from the display shielding area storing unit, corresponding to the detected state and to generate data of a display shielding image for shielding the read display shielding area.

10. A security managing system that includes an operation terminal having an input device and a display device, which is able to shift a step-by-step process status having a plurality of process application execution states from one state to another, the states including an image photographing process application execution state, a patient registration process application execution state, an image observation process application execution state, and a filing process application execution state, the security managing system comprising:

a part-screen saver shape storing unit configured to store part-screen saver image shapes of the respective states, wherein each part-screen saver image shape is to shield a part of a screen of the display device;

an event detecting unit configured to detect an event not to use the operation terminal for a fixed time;

a process application execution state detecting unit configured to detect a process application execution state of the operation terminal;

a part-screen saver managing unit configured to perform, when the event is detected by the event detecting unit, a generation requirement of the part-screen saver with the detected state; and a part-screen saver image generating unit configured to read data of a screen saver image shape from the part-screen saver shape storing unit, corresponding to the detected state based on the generation requirement, and to generate data of a part-screen saver image for shielding the read screen saver image shape.

11. A security managing method that includes an operation terminal having an input device and a display device, which is able to shift a step-by-step process status having a plurality of process application execution states from one state to another, the states including an image photographing process application execution state, a patient registration process application execution state, an image observation process application execution state, and a filing process application execution state, the security managing method comprising:

storing display shielding areas of the respective states, which are within a screen of the display device in which display shielding is activated;

detecting an event not to use the operation terminal for a fixed time;

detecting a process application execution state of the operation terminal;

reading, when the event is detected, data of a display shielding area corresponding to the detected state; and generating data of a display shielding image for shielding the read display shielding area.

12. A security managing method that includes an operation terminal having an input device and the display device, which is able to shift a step-by-step process status having a plurality of process application execution states from one state to another, the states including an image photographing process application execution state, a patient registration process application execution state, an image observation process application execution state, and a filing process application execution state, the security managing method comprising:

storing part-screen saver image shapes of the respective states, wherein each part-screen saver image shape is to shield a part of a screen of the display device;

detecting an event not to use the operation terminal for a fixed time;

detecting a process application execution state of the operation terminal when the event is detected; and generating data of a part-screen saver image using data of a part-screen saver image shape corresponding to the detected state.

13. A security managing method for a medical image diagnostic apparatus that includes an operation terminal having an inputting device and a display device, which is able to shift a step-by-step process status having a plurality of process application execution states from one state to another, the states including an image photographing process application execution state, a patient registration process application execution state, an image observation process application execution state, and a filing process application execution state, the security managing method comprising:

storing display shielding areas of the respective states, which are within a screen of the display device, in which display shielding is activated;

detecting an event not to use the operation terminal for a fixed time;

detecting a process application execution state of the operation terminal;

reading, when the event is detected, data of a display shielding area corresponding to the detected state; and generating data of a display shielding image for shielding the read display shielding area.

14. A security managing method for a medical image diagnostic apparatus that includes an operation terminal having an inputting device and a display device, which is able to shift a step-by-step process status having a plurality of process application execution states from one state to another, the states including an image photographing process application execution state, a patient registration process application execution state, an image observation process application execution state, and a filing process application execution state, the security managing method comprising:

storing part-screen saver image shapes of the respective states, wherein each part-screen saver image shape shields a part of a screen of the display device;

detecting an event not to use the operation terminal for a fixed time;

detecting a process application execution state of the operation terminal when the event is detected; and generating data of a part-screen saver image using data of a part-screen saver image shape corresponding to the detected state.

* * * * *